(12) United States Patent
Adelman et al.

(10) Patent No.: US 10,753,921 B2
(45) Date of Patent: Aug. 25, 2020

(54) ASSAY APPARATUS

(71) Applicant: iAssay, Inc., San Diego, CA (US)

(72) Inventors: Lonnie W. Adelman, La Jolla, CA (US); Nitin C. Bhagwath, Santa Clara, CA (US)

(73) Assignee: iAssay, Inc., San Diego, CA (US)

( * ) Notice: Subject to any disclaimer, the term of this patent is extended or adjusted under 35 U.S.C. 154(b) by 0 days.

(21) Appl. No.: 16/380,861

(22) Filed: Apr. 10, 2019

(65) Prior Publication Data
US 2019/0234929 A1 Aug. 1, 2019

Related U.S. Application Data

(63) Continuation of application No. 14/651,167, filed as application No. PCT/US2013/074209 on Dec. 10, 2013, now Pat. No. 10,309,954.

(Continued)

(51) Int. Cl.
*G01N 33/487* (2006.01)
*H04W 12/02* (2009.01)
(Continued)

(52) U.S. Cl.
CPC ....... *G01N 33/487* (2013.01); *A61B 5/02055* (2013.01); *G01N 21/25* (2013.01); *G01N 21/6486* (2013.01); *G01N 33/48785* (2013.01); *G01N 33/497* (2013.01); *H04W 4/80* (2018.02); *H04W 12/02* (2013.01); *A61B 5/0059* (2013.01);
(Continued)

(58) Field of Classification Search
CPC .... G01N 33/53; G01N 33/48; G01N 21/6486; G06F 19/3406
See application file for complete search history.

(56) References Cited

U.S. PATENT DOCUMENTS

| | | | |
|---|---|---|---|
| 6,503,555 B1 | 1/2003 | Katta et al. | |
| 6,699,188 B2 | 2/2004 | Wessel | |

(Continued)

FOREIGN PATENT DOCUMENTS

| | | |
|---|---|---|
| EP | 1147739 A2 | 10/2001 |
| EP | 1403795 A1 | 3/2004 |

(Continued)

OTHER PUBLICATIONS

Hai Hu, "DW4TR: A Data Warehouse for Translational Research", journal of Biomedical Informatics 44 (2011) 1004-1019 (Year: 2011).*

(Continued)

*Primary Examiner* — Maurice C Smith
(74) *Attorney, Agent, or Firm* — Wagenknecht IP Law Group, PC

(57) ABSTRACT

Provided herein is an assay apparatus comprising at least one assay module; and a portable frame adapted to releasably retain the at least one assay module. The at least one assay module is adapted to perform at least one assay. The assay module comprises a sample receiver and an assay device operatively associated with the sample receiver. In some embodiments, the assay apparatus further comprises at least one functional module releasably retained by the portable frame. The functional module is operatively associated with the assay module when retained by the portable frame.

18 Claims, 5 Drawing Sheets

Related U.S. Application Data

(60) Provisional application No. 61/797,691, filed on Dec. 12, 2012.

(51) Int. Cl.

| | | |
|---|---|---|
| *H04W 4/80* | (2018.01) | |
| *A61B 5/0205* | (2006.01) | |
| *G01N 21/25* | (2006.01) | |
| *G01N 21/64* | (2006.01) | |
| *G01N 33/497* | (2006.01) | |
| *H04W 12/08* | (2009.01) | |
| *A61B 5/00* | (2006.01) | |
| *A61B 5/01* | (2006.01) | |
| *A61B 5/021* | (2006.01) | |
| *A61B 5/024* | (2006.01) | |
| *A61B 5/08* | (2006.01) | |
| *A61B 5/1455* | (2006.01) | |
| *H04W 88/06* | (2009.01) | |

(52) U.S. Cl.
CPC .............. *A61B 5/0071* (2013.01); *A61B 5/01* (2013.01); *A61B 5/021* (2013.01); *A61B 5/02438* (2013.01); *A61B 5/0816* (2013.01); *A61B 5/1455* (2013.01); *A61B 5/6898* (2013.01); *H04W 12/08* (2013.01); *H04W 88/06* (2013.01)

(56) References Cited

U.S. PATENT DOCUMENTS

| | | | |
|---|---|---|---|
| 8,172,761 B1 | 5/2012 | Rulkov et al. | |
| 8,675,356 B2* | 3/2014 | Strauser | G06F 1/1632 361/679.4 |
| 9,425,651 B2* | 8/2016 | Strauser | H02J 7/0027 |
| 9,685,803 B2* | 6/2017 | Strauser | H02J 7/0027 |
| 10,309,954 B2 | 6/2019 | Adelman et al. | |
| 2003/0141358 A1 | 7/2003 | Hudson et al. | |
| 2005/0137481 A1 | 6/2005 | Sheard et al. | |
| 2005/0203353 A1 | 9/2005 | Ma et al. | |
| 2006/0222567 A1 | 10/2006 | Kloepfer et al. | |
| 2007/0190525 A1 | 8/2007 | Gu et al. | |
| 2008/0161661 A1* | 7/2008 | Gizewski | A61B 5/0059 600/306 |
| 2008/0288178 A1 | 11/2008 | Frazier | |
| 2009/0054741 A1* | 2/2009 | McAleer | A61B 5/0205 600/301 |
| 2009/0282192 A1 | 11/2009 | Maus et al. | |
| 2010/0222648 A1 | 9/2010 | Tan | |
| 2010/0249965 A1 | 9/2010 | Rao et al. | |
| 2010/0309454 A1 | 12/2010 | Zhang | |
| 2011/0038765 A1 | 2/2011 | Drucker et al. | |
| 2011/0201099 A1* | 8/2011 | Anderson | G01N 21/05 435/287.2 |
| 2012/0095309 A1 | 4/2012 | Price et al. | |
| 2012/0113422 A1 | 5/2012 | Kivioja et al. | |
| 2012/0123686 A1* | 5/2012 | Xiang | G16H 40/63 702/19 |
| 2012/0149035 A1 | 6/2012 | Burd et al. | |
| 2012/0308444 A1 | 12/2012 | Zhu | |
| 2013/0114203 A1* | 5/2013 | Ignatchenko | G06F 1/1632 361/679.41 |
| 2013/0179176 A1 | 7/2013 | Gotthardt | |
| 2013/0224767 A1 | 8/2013 | Arai | |
| 2014/0242612 A1 | 8/2014 | Wang et al. | |

FOREIGN PATENT DOCUMENTS

| | | |
|---|---|---|
| WO | 19992236 A1 | 5/1999 |
| WO | 2010004241 A1 | 1/2010 |
| WO | 2014093397 A1 | 6/2014 |

OTHER PUBLICATIONS

Mudanyali et al. "Integrated Rapid-Diagnostic-Test Reader Platform on a Cellphone." Lab on a Chip, Aug. 7, 2012, 12(15):2678-2686.

PCT/US2013/074209 International Preliminary Report on Patentability dated Jun. 25, 2015.

PCT/US2013/074209 International Search Report and Written Opinion dated Mar. 14, 2014.

* cited by examiner

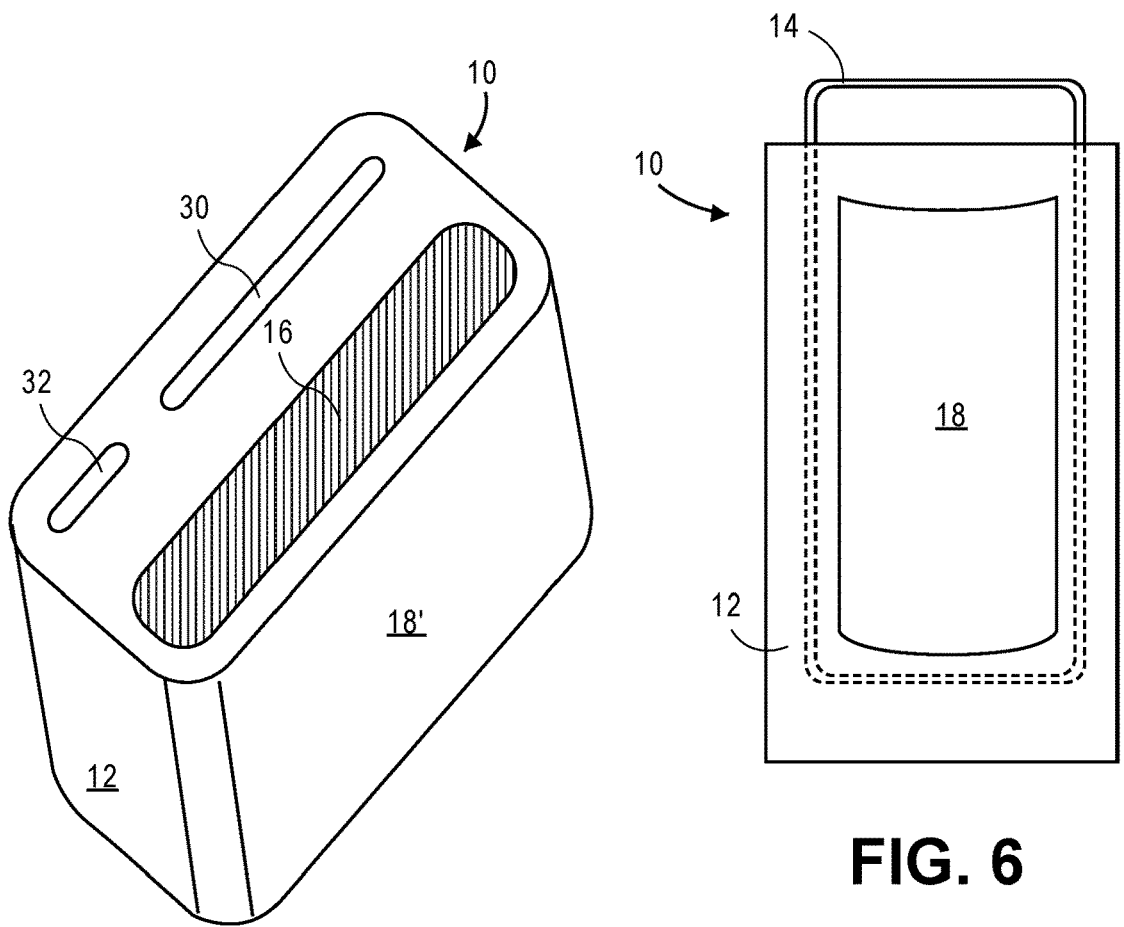
FIG. 7
FIG. 6
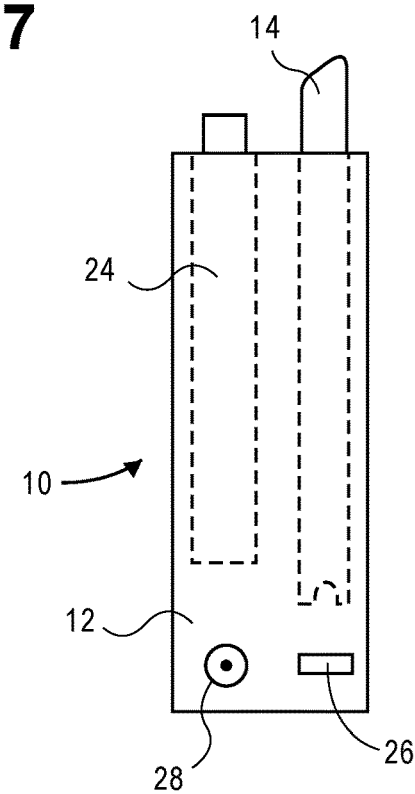
FIG. 8

ASSAY APPARATUS

CROSS-REFERENCE TO RELATED APPLICATIONS

This application is a continuation of U.S. application Ser. No. 14/651,167, filed Jun. 10, 2015, which claims the benefit of priority of PCT/US2013/074209, filed on Dec. 10, 2013, and U.S. Provisional Application No. 61/797,691, filed on Dec. 12, 2012, the contents of each of which are incorporated herein in their entirety.

BACKGROUND OF THE DISCLOSURE

There is a need for portable assay apparatus and methods that can conveniently and effectively provide on-site assay results and/or communicate assay results to a user.

SUMMARY OF THE DISCLOSURE

Provided herein is an assay apparatus comprising at least one assay module; and a portable frame adapted to releasably retain the at least one assay module. The at least one assay module is adapted to perform at least one assay. The assay module comprises a sample receiver and an assay device operatively associated with the sample receiver.

In some embodiments, the assay apparatus further comprises at least one functional module releasably retained by the portable frame. The functional module is operatively associated with the assay module when retained by the portable frame.

In some embodiments, the at least one functional module comprises a functional device selected from the group consisting of a battery, a wireless data transmission device, a wired data transmission device, a microprocessor, an interface for receiving and recording signals from at least one vital sign detector, a luminescence recorder, a display device, a portable computing device, a data storage device, and combinations thereof.

In some embodiments, the at least one functional module comprises a battery, and wherein the assay module further comprising a power inlet for receiving electric power from the battery.

In some embodiments, the at least one functional module comprises a wireless data transmission device. In some embodiments, the wireless data transmission device operates on one or more transmission technologies selected from 3G communication protocols, 4G communication protocols, GSM standards, CDMA protocols, IEEE 802.11 standards, Bluetooth protocols, satellite communications, visible light communications, infrared communications, and near field communications. In some embodiments, the wireless data transmission device is adapted to transmit date to a local area network or the Internet.

In some embodiments, the at least one functional module comprises a wired data transmission device to connect to a local area network or the Internet through wired data transmission.

In some embodiments, the wireless data transmission device and/or the wired data transmission device is a portable computing device. In some embodiments, the portable computing device is a smart phone or a tablet computer.

In some embodiments, the at least one functional module comprises a microprocessor. In some embodiments, the microprocessor is a quad-core microprocessor.

In some embodiments, the at least one functional module comprises an interface for at least one vital sign detector operative associated with the functional module. In some embodiments, the at least one vital sign detectors collects body temperature, heart rate, blood pressure, respiratory rate, or combinations thereof.

In some embodiments, the at least one functional module comprises a luminescence recorder adapted to record luminescence generated by the assay device. The luminescence recorder optionally includes an auxiliary illumination source for providing illumination at the desired wavelength(s), e.g. the operational wavelength(s) of the luminescence recorder. In some embodiments, the luminescence recorder is selected from a camera, a fluorescent light recorder, a UV recorder, a diode/amplifier type receiver, or combinations thereof. In some embodiments, the luminescence recorder is a built-in camera of a portable computing device.

In some embodiments, the at least one functional module comprises a display device adapted to display assay module information, functional module information, sample information, or combinations thereof. In some embodiments, the display device is a high-resolution display device. In some embodiments, the high-resolution display device further comprises a touch screen overlay. In some embodiments, the display device is a display window of a portable computing device.

In some embodiments, the portable computing device is selected from a smart-phone or a tablet computer. In some embodiments, the portable computing device comprises a software module configured to provide step-by-step guidance for using the assay apparatus. In some embodiments, the portable computing device comprises a software module configured to collect, process and organize assay information acquired from the assay module, the functional module, or a combination thereof. In some embodiments, the portable computing device comprises software module configured to communicate assay information to a user, wherein the assay information is acquired from the assay module, the functional module, or a combination thereof. In some embodiments, the assay information is securely communicated to the user through a server. In some embodiments, the server is an Internet server or a local access network server. In some embodiments, the user is a patient, a doctor, or a nurse.

In some embodiments, the data storage device is configured to store assay information acquired from the assay module, the functional module, or a combination thereof.

In some embodiments, the at least one assay performed by the assay module is selected from the group consisting of health care assays, veterinary assays, food product assays, and environmental assays.

In some embodiments, the at least one assay is selected from the group consisting of Sodium assay, Potassium assay, Chloride assay, BUN/Urea assay, Glucose assay, Hematocrit assay, Ionized Calcium assay, PO2 assay, pH assay, PCO2 assay, Creatinine assay, Lactate assay, Celite ACT assay, Prothrombin Time PT/INR assay, Kaolin ACT assay, Cardiac Troponin I/cTnI assay, Total Carbon Dioxide/TCO2 assay, Creatine Kinase MB/CK-MB assay, and B-Type Natriuretic Peptide/BNP assay.

In some embodiments, the at least one assay is selected from immunodiagnostic assays, DNA sequencing assays, bioluminescent assays, cell cytometry assays, lateral flow assays, and HbA1c assays.

In some embodiments, the immunodiagnostic assays are enzyme-linked immunosorbent assays (ELISA).

In some embodiments, the DNA sequencing assays are based on DNA sequencing chips and wherein the assay device comprises interface to the DNA sequencing chip.

In some embodiments, the at least one assay is a bioluminescence assay and wherein the assay device comprises an optical device for detecting bioluminescence, and a display device for visualizing the detected bioluminescence.

In some embodiments, the at least one assay is a cell cytometry assay, and wherein the assay device comprises a micro-laser, a microcomputer, and an optical sensor.

In some embodiments, the at least one assay is a lateral flow assay based on comparison of line intensity, line color, or a combination thereof to one or more reference lines. In some embodiments, the lateral flow assay is selected from pregnancy assays or drug screening assays.

In some embodiments, the assay device comprises an optical device disposed for imaging the lateral flow assay, and a display device for visualizing the image of the lateral flow assay.

In some embodiments, the at least one assay is an HbA1c assay based on immunoassay or boronate affinity chromatograph.

In some embodiments, the at least one assay is an environmental assay selected from air quality assays, asbestos assays, water quality assays, soil content assays, or radon gas assays. In some embodiments, the at least one assay is an environmental assay and the assay device comprises gas chromatography (GC).

In some embodiments, the portable frame comprises a plurality of recessed receiving areas for releasably receiving the at least one assay module and the at least one functional module.

In some embodiments, the portable frame further comprises a power inlet for receiving electricity from a power source, and wherein at least one of the recessed receiving areas is electrically connected to the power inlet. In some embodiments, at least two of the recessed receiving areas are electrically connected to each other to allow electrical power transfer between assay modules, between functional modules, or between assay and functional modules.

In some embodiments, the portable frame further comprises a data inlet for receiving data from a data source, and wherein at least one of the recessed receiving areas is connected to the data inlet through a data cable. In some embodiments, at least two of the recessed receiving areas are connected to each other through a data cable to allow data transfer between assay modules, between functional modules, or between assay and functional modules.

In some embodiments, at least two of the recessed receiving areas are optically connected to each other to allow transfer of light or optical information between assay modules, between functional modules, or between assay and functional modules. In some embodiments, the at least two of the recessed receiving areas are optically connected to each other through at least one light channel, at least one optical fiber connector, at least one optical lens, or combinations thereof. In some embodiments, the optical connection is integrated to the portable frame.

In some embodiments, the assay apparatus further comprises a module-recognizing mechanism configured to prevent unauthorized use of the assay apparatus. In some embodiments, the module-recognizing mechanism comprises one or more physical features on the at least one assay module and one or more matching physical feature on the portable frame. In some embodiments, the at least one assay module is allowed to perform the at least one assay upon matching of the one or more physical features on the at least one assay module and the portable frame. In some embodiments, the at least one assay module is allowed to perform the at least one assay upon matching of the one or more physical features on the at least one assay module and the portable frame and upon breaking of the one or more physical features on the at least one assay module. In some embodiments, the module-recognizing mechanism comprises security hologram.

Also provided herein is an assay apparatus comprising an assay module adapted to perform an interactive assay comprising multiple assay steps, and a portable frame adapted to releasably retain the assay module. The assay module comprises a sample receiver, an interactive assay device operatively associated with the sample receiver. The interactive assay device comprises at least one check point adapted to allow selective continuation of the remaining assay steps.

In some embodiments, the interactive assay device comprises an optical device configured to collect assay information the at least one check point. In some embodiments, the optical device generates an image of the at least one check point. In some embodiments, the optical device generates a signal reflecting assay information collected at the check-point.

In some embodiments, the selective continuation of the remaining assay steps is controlled by a user. In some embodiments, the selective continuation of the remaining assay steps is controlled by a microprocessor.

In some embodiments, the interactive assay comprises at least one immunodiagnostic assay. In some embodiments, the interactive assay device comprising microfluidic channels.

In some embodiments, the assay apparatus further comprises a module-recognizing mechanism configured to prevent unauthorized use of the assay apparatus. In some embodiments, the module-recognizing mechanism comprises one or more physical features on the assay module and one or more matching physical feature on the portable frame. In some embodiments, the assay module is allowed to perform the at least one assay upon matching of the one or more physical features on the assay module and the portable frame. In some embodiments, the at least one assay module is allowed to perform the interactive assay after matching of the one or more physical features on the assay module and the portable frame and upon breaking of the one or more physical features on the assay module. In some embodiments, the module-recognizing mechanism comprises security hologram. In some embodiments, the module-recognizing mechanism comprises data encryption. In some embodiments, the module-recognizing mechanism comprises a combination of security hologram and data encryption.

BRIEF DESCRIPTION OF THE DRAWINGS

The features of the disclosed assay apparatus, systems, and methods are set forth with particularity in the appended claims. A better understanding of the features of the present disclosure will be obtained by reference to the following detailed description that sets forth illustrative embodiments, in which the principles of the invention are utilized, and the accompanying drawings of which:

FIG. 6 is a front elevation view of an assay apparatus embodying the principals of the invention;

FIG. 7 is a top perspective view of the embodiment of FIG. 6 showing the several apertures included in the assay apparatus;

FIG. 8 is a side elevation view of the embodiment of FIG. 6 showing a smartphone and an assay inserted in the assay apparatus.

It should be understood that the drawings are not necessarily to scale and that the disclosed embodiments are sometimes illustrated diagrammatically and in partial views. In certain instances, details which are not necessary for an understanding of the disclosed device or method which render other details difficult to perceive may have been omitted. It should be understood, of course, that this disclosure is not limited to the particular embodiments illustrated herein.

DETAILED DESCRIPTION OF THE INVENTION

The present disclosure is described in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations and variations thereof Assay Apparatus According to one aspect of the present disclosure, an assay apparatus is provided as comprising at least one assay module; and a portable frame adapted to releasably retain the at least one assay module. The at least one assay module is adapted to perform at least one assay. The assay module comprises a sample receiver and an assay device operatively associated with the sample receiver. In some embodiments, the assay apparatus further comprises at least one functional module releasably retained by the portable frame. The functional module is operatively associated with the assay module when retained by the portable frame.

Without wishing to be bound by any particular theory, the technical features of the assay apparatus disclosed herein improve portability, efficiency, adaptability, accuracy, and/or security of existing on-site assay apparatus and methods, an insight heretofore unknown in the technical field. The term "portable" as used in the present disclosure refers to the capability of being operated while being held in the hands of an operator. It is to be understood that the disclosed apparatus is also capable of being operated while the apparatus is supported by or rested on an inanimate surface, such as on a patient's bed, on a desk or chair, on a utility cart, or any such surfaces located at or close to the site where the assay takes place.

Figure 2:
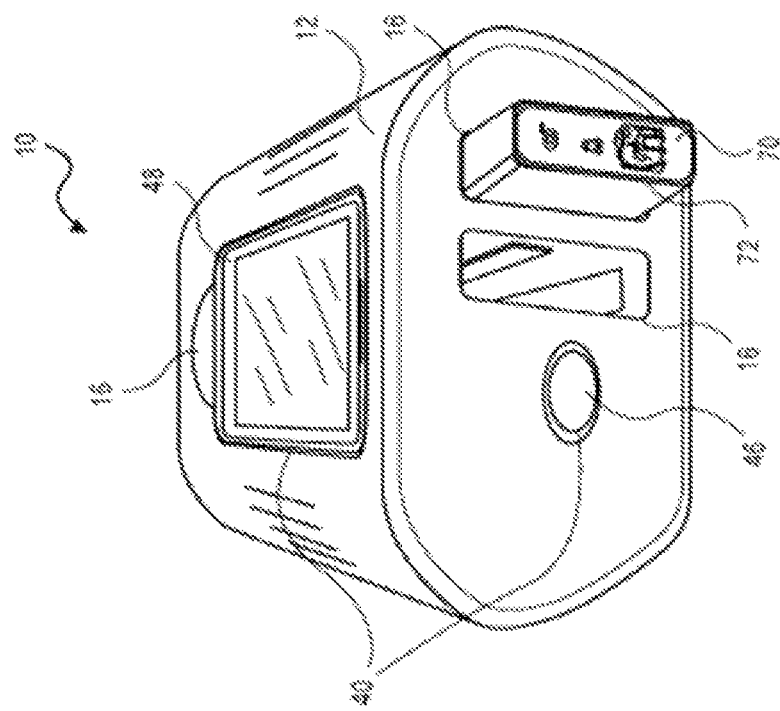
FIG. 2 is a side perspective view of an assay apparatus according to the present disclosure.
Figure 1:
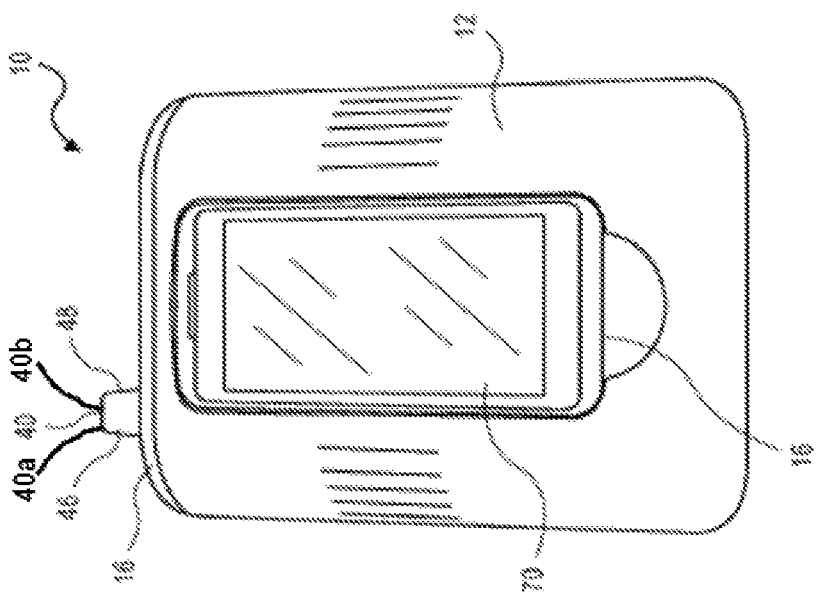
FIG. 1 is a front perspective view of an assay apparatus according to the present disclosure.

Referring now to FIGS. 1-2, a non-limiting example of the assay apparatus 10 is illustrated as including at least one assay module 40 and a portable frame 12 adapted to releasably retain the at least one assay module 40. In some embodiments, the portable frame 12 includes one or more recessed received areas 16 in which the assay module 40 can be releasably retained. The assay module 40 is adapted to perform at least one assay and includes a sample receiver 46 and an assay device 48 operatively associated with the sample receiver 46. In some embodiments, the sample receiver 46 is a sample receiving slot or sample receiving opening provided on the assay module 40 or on the assay apparatus 10.

Still referring to FIGS. 1-2, the assay apparatus 10 further comprises at least one functional module 70 releasably retained by the portable frame 12. The functional module 70 is operatively associated with the assay module 40 when retained by the portable frame. In some embodiments, the portable frame 12 includes one or more recessed received areas 16 in which the functional module 70 can be releasably retained. In some embodiments, the functional module 70 does not include an sample receiver for receiving assay sample, but functions to operate the assay module 40, to improve performance of the assay module 40, to supplement the assay module 40, and/or to provide auxiliary functions to the assay apparatus 10 that is not directly related to the operation of the assay module 40.

In some embodiments, the sample receiver 46 and assay device 48 are integrated to form a one-piece assay module 40, as shown in FIG. 1. In some embodiments, the sample receiver 46 and assay device 48 form a two-piece assay module 40, as shown in FIG. 2. As a non-limiting example illustrated in FIG. 2, the sample receiver 46 is a sample slot provided on the portable frame 12 and the assay device 48 is an optical device, such as a built-in camera of a portable computing device (e.g. smartphone).

The sample receiver 46 and assay device 48 are operationally associated with each other so that the assay information can be collected by the assay device 48. In some embodiments, the assay device 48 performs the assay by collecting optical information from the sample receiver. In some embodiments, the assay device 48 performs the assay by collecting bioluminescence information from the sample receiver. In some embodiments, the assay device 48 performs the assay by collecting magnetic (e.g. reading or monitoring of a magnetic field bound to target moieties or analytes) or electromagnetic information from the sample receiver. In some embodiments, the sample receiver 46 is in fluid communication with the assay device 48 so that analytes of the assay can be transferred to the assay device for analysis and assay information collection (e.g. chromatography, electrophoresis, etc.).

The functional module 70 and the assay module 40 are also operationally associated with each other. In some embodiments, the functional module 70 and the assay module 40 are electrically associated with each other. In some embodiments, the portable frame further comprises a power inlet for receiving electricity from a power source, and wherein at least one of the recessed receiving areas is electrically connected to the power inlet. In some embodiments, at least two of the recessed receiving areas are electrically connected to each other to allow electrical power transfer between assay modules, between functional modules, or between assay and functional modules.

In some embodiment, the functional module 70 and the assay module 40 are connected with each other through wireless data transmission, such as through Bluetooth or similar data communication technologies. In some embodiment, the functional module 70 and the assay module 40 are connected with each other through wired data transmission, such as through data cables. In some embodiments, the portable frame further comprises a data inlet for receiving data from a data source, and wherein at least one of the recessed receiving areas is connected to the data inlet through a data cable. In some embodiments, at least two of the recessed receiving areas are connected to each other through a data cable to allow data transfer between assay modules, between functional modules, or between assay and functional modules.

In some embodiments, the functional module 70 and the assay module 40 are optically associated with each other. In some embodiments, at least two of the recessed receiving areas are optically connected to each other to allow light transfer between assay modules, between functional modules, or between assay and functional modules. In some embodiments, two or more recessed receiving areas are optically connected together by one or more light channels, one or more optical fiber connectors, optical lenses, or combinations thereof.

In some embodiments, the portable frame 12 further optionally includes at least one built-in assay device operatively associated with the assay module, the functional module, or both. In some embodiments, the built-in assay device is a built-in optical assay device, such as a built-in camera (with or without auxiliary light source).

Assay Module

Figure 3:
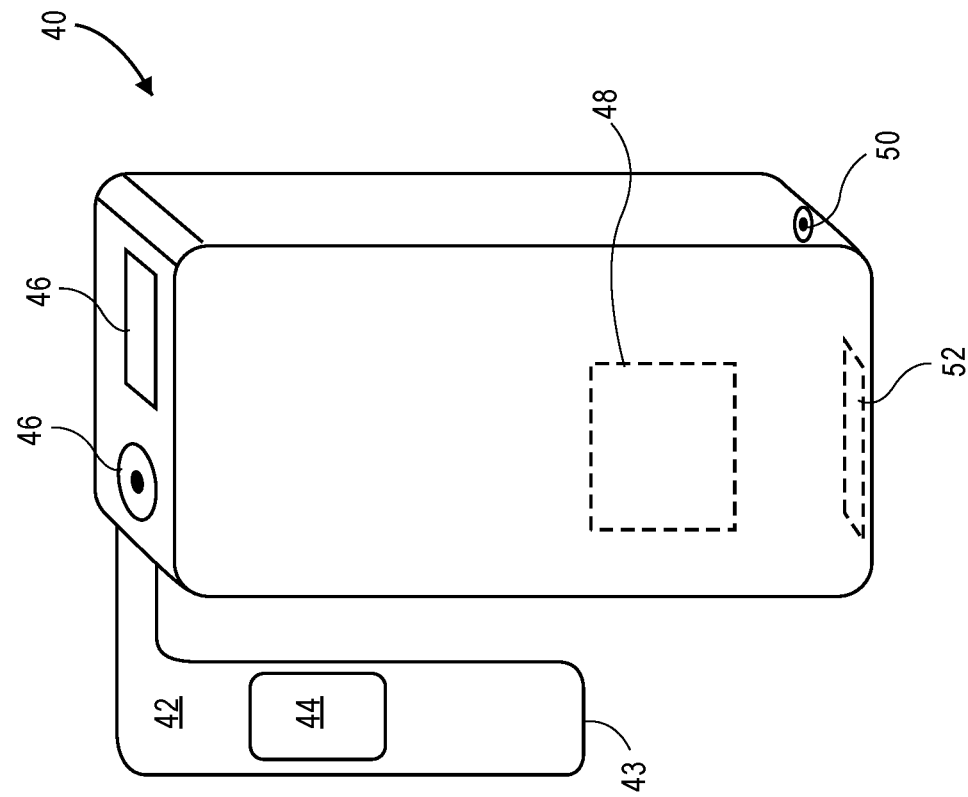
FIG. 3 is a front elevation view of an assay module according to the present disclosure.

Turning now to FIG. 3, a non-limiting example of the one-piece assay module 40 is illustrated as including one or more sample slots 46, an optical assay device 48, and an optional DC port 50 for receiving power. The assay module 40 also includes an optional connector 52 that is engaged when the connector is positioned within the recessed receiving are 16. The optical assay device 48 can be replaced with electronic assay device, bioluminescence assay device, chromatography assay device, etc., depending on the type of assay performed.

The assay module 40 according to the present disclosure can perform many assays. In some embodiments, the at least one assay performed by the assay module is selected from the group consisting of health care assays, veterinary assays, food product assays, and environmental assays.

In some embodiments, the at least one assay is selected from the group consisting of Sodium assay, Potassium assay, Chloride assay, BUN/Urea assay, Glucose assay, Hematocrit assay, Ionized Calcium assay, PO2 assay, pH assay, PCO2 assay, Creatinine assay, Lactate assay, Celite ACT assay, Prothrombin Time PT/INR assay, Kaolin ACT assay, Cardiac Troponin I/cTnI assay, Total Carbon Dioxide/TCO2 assay, Creatine Kinase MB/CK-MB assay, and B-Type Natriuretic Peptide/BNP assay.

In some embodiment, the at least one assay is selected from the group consisting of HbAlc assay, Albumin/Creatinine Ratio (ACR) urine assay, Insulin-like Growth Factor Binding Protein-1 (IGFBP-1) assay, phosphorylated IGFBP-1 assay, *Wuchereria bancrofti* antigen assay, G6PD enzyme assay, influenza A and B nucleoprotein antigens assay, *Legionella pneumophila* serogroup 1 antigen assay, *Plasmodium* antigens assay, respiratory syncytial virus (RSV) fusion protein antigen assay, *Staphylococcus aureus* assay, *Streptococcus pyogenes* Group A antigen assay, *S. pneumoniae* antigen assay, cholesterol assay, triglyceride assay, glucose assay, HIV assay, HIV-1/2 assay, *Treponema pallidum* antibody assay, LAM antigen (lipoarabinomannan) assay, HBsAg assay, human chorionic gonadotropin (hCG) assay, nuclear mitotic apparatus protein (NuMA) assay, penicillin binding protein 2a (PBP2a) assay, CD4 T-cell assay, BNP assay, CK-MB assay, d-dimer assay, myoglobin assay, NGAL assay, troponin I assay, qualitative TOX Drug Screen assay, *H. pylori* antibody assay, faecal occult blood assay, *Plasmodium falciparum* (P.f), *Plasmodium vivax* (P.v.), *Plasmodium malariae* (P.m) and *Plasmodium ovale* (P.o.) antigens assay, respiratory syncytial virus (RSV) assay, infectious mononucleosis heterophile antibodies assay, luteinizing hormone (LH) assay, Chlamydia trachomatis antigen assay, human anti-*S. cerevisiaes* antibodies assay, glutamate dehydrogenase (GDH) assay, *C. difficile* toxin B assay, *Cryptosporidium* oocyst antigens assay, *Entamoeba histolytica* adhesion assay, *Giardia lamblia* assay, *Giardia* cyst antigen assay, *Cryptosporidium oocyst* antigen assay, fecal lactoferrin assay, fecal VTEC/STEC toxins assay, cross-linked N-telopeptides of bone type I collagen (NTx) assay, arthropod-borne viruses assay, histone antibody assay, and Ribosomal P antibodies.

In some embodiments, the at least one assay is an HbAlc assay based on immunoassay or boronate affinity chromatograph.

In some embodiments, the at least one assay is selected from immunodiagnostic assays, DNA sequencing assays, bioluminescent assays, cell cytometry assays, and lateral flow assays.

Immunodiagnostic Assay

Immunodiagnostics is a diagnostic methodology that uses an antigen-antibody reaction as their primary means of detection. It is suitable for the detection of small amounts of (bio)chemical substances. Antibodies specific for a desired antigen can be conjugated with a radiolabel, fluorescent label, or color-forming enzyme and are used as a "probe" to detect it. Well known applications include pregnancy tests, immunoblotting, ELISA and immunohistochemical staining of microscope slides. The speed, accuracy and simplicity of such tests contribute to the development of rapid techniques for the diagnosis of disease, microbes and even illegal drugs in vivo (of course tests conducted in a closed environment have a higher degree of accuracy). Such testing is also used to distinguish compatible blood types.

In some embodiments, the immunodiagnostic assays are enzyme-linked immunosorbent assays (ELISA). The ELISA (sometimes also called an EIA) is a sensitive, inexpensive assay technique involving the use of antibodies coupled with indicators (e.g. enzymes linked to dyes) to detect the presence of specific substances, such as enzymes, viruses, or bacteria. While there are several different types, basically ELISAs are created by coating a suitable plastic (the solid phase) with an antibody. To complete the reaction, a sample believed to contain the antigen of interest is added to the solid phase. Then a second antibody coupled with an enzyme is used followed by the addition of a color-forming substrate specific to the antibody.

In some embodiments, the ELISA assay is based on comparison of color type, color intensity, or a combination thereof to one or more references. In some embodiments, the assay device comprises an optical device disposed for imaging or analyzing the ELISA assay, and optionally a display device for visualizing the image of the ELISA assay.

In some embodiments, the immunodiagnostic assays are lateral flow assays. Lateral flow tests also known as Lateral Flow Immunochromatographic Assays are simple devices intended to detect the presence (or absence) of a target analyte in sample (matrix) without the need for specialized and costly equipment, though many lab based applications exist that are supported by reading equipment. Typically, these tests are used for medical diagnostics either for home testing, point of care testing, or laboratory use. A widely spread and well known application is the home pregnancy test.

The lateral flow test is based on a series of capillary beds, such as pieces of porous paper or sintered polymer. Each of these elements has the capacity to transport fluid (e.g., urine) spontaneously. The first element (the sample pad) acts as a sponge and holds an excess of sample fluid. Once soaked, the fluid migrates to the second element (conjugate pad) in which the manufacturer has stored the so-called conjugate, a dried format of bio-active particles (see below) in a salt-sugar matrix that contains everything to guarantee an optimized chemical reaction between the target molecule (e.g., an antigen) and its chemical partner (e.g., antibody) that has been immobilized on the particle's surface. While the sample fluid dissolves the salt-sugar matrix, it also dissolves the particles and in one combined transport action the sample and conjugate mix while flowing through the porous structure. In this way, the analyte binds to the particles while migrating further through the third capillary bed. This material has one or more areas (often called stripes) where a third molecule has been immobilized by the manufacturer. By the time the sample-conjugate mix reaches these strips, analyte has been bound on the particle and the third 'capture' molecule binds the complex. After a while, when more and more fluid has passed the stripes, particles accumulate and the stripe-area changes color. Typically there are at least two stripes: one (the control) that captures any particle and thereby shows that reaction conditions and technology worked fine, the second contains a specific capture molecule and only captures those particles onto which an analyte molecule has been immobilized. After passing these reaction zones the fluid enters the final porous material that acts as a waste container. Lateral Flow Tests can operate as either competitive or sandwich assays.

Figure 5:
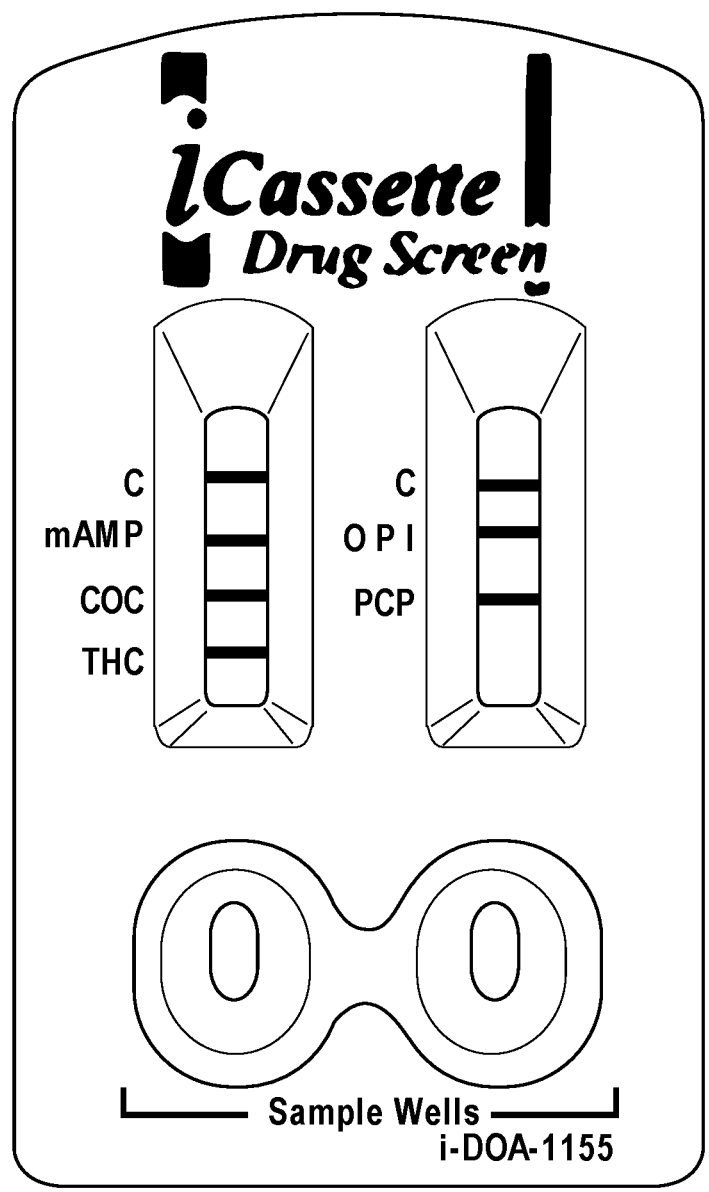
FIG. 5 is a front elevation view of a conventional lateral flow assay device.

In some embodiments, the lateral flow assay based on comparison of line intensity, line color, or a combination thereof to one or more reference lines. In some embodiments, the assay device comprises an optical device disposed for imaging or analyzing the lateral flow assay, and optionally a display device for visualizing the image of the lateral flow assay. A non-limiting example of a lateral flow assay sample is illustrated in FIG. 5.

DNA Sequencing Assay

In some embodiments, the DNA sequencing assays are based on DNA sequencing chips and wherein the assay device comprises interface to the DNA sequencing chip.

Genome sequencing is a costly but important tool in biomedical research used for the study of genetic disease and cancer. Common sequencing methods only sequence one or two DNA bases at a time in several cycles, which makes them costly to run in terms of time and reagents required. Recent development in this area includes a sequencing technique called sequencing by denaturation (SBD), which can be performed on a chip with a single integrated microfluidic device.

On the device, fluorescently labeled nucleotides are randomly incorporated into the DNA during replication. This results in fragments of different lengths, each labeled with a fluorescent molecule corresponding to its ending base type. Next these fragments are heated and, because shorter fragments have a lower melting temperature, sequentially denatured from the shortest fragment to the longest. By monitoring the decrease in fluorescence during this process, the signal can be analyzed to determine the base sequence of the target DNA template.

The technical features of SBD include the short sequencing run, low cost reagents and its ease of use. The device has the capability for performing high-speed fluorescence imaging while biomedical reactions occurs in a controlled manner Due to its relative simplicity, SBD can bring down the cost of large-scale sequencing drastically.

Bioluminescence Assay

In some embodiments, the at least one assay is a bioluminescence assay and wherein the assay device comprises an optical device for detecting bioluminescence, and a display device for visualizing the detected bioluminescence. In some embodiment, the bioluminescence assay is based on luciferase, which is a generic term for the class of oxidative enzymes used in bioluminescence and is distinct from a photoprotein.

In biological research, luciferase is commonly used as a reporter to assess the transcriptional activity in cells that are transfected with a genetic construct containing the luciferase gene under the control of a promoter of interest. Additionally proluminescent molecules that are converted to luciferin upon activity of a particular enzyme can be used to detect enzyme activity in coupled or two-step luciferase assays. Such substrates have been used to detect caspase activity and cytochrome P450 activity, among others.

Luciferase can also be used to detect the level of cellular ATP in cell viability assays or for kinase activity assays. Luciferase can act as an ATP sensor protein through biotinylation. Biotinylation will immobilize luciferase on the cell-surface by binding to a streptavidin-biotin complex. This allows luciferase to detect the efflux of ATP from the cell and will effectively display the real-time release of ATP through bioluminescence. Luciferase can additionally be made more sensitive for ATP detection by increasing the luminescence intensity through genetic modification.

One example of bioluminescence ATP assay is the ATP Bioluminescence Assay Kit CLS II by Roche Applied Science, which is specially developed for applications in which constant light signals are required for kinetic studies of enzymes and metabolic studies, or if coupled enzymatic assays are applied. If ATP determinations are manually started, the CLS Kit provides high reproducibility due to the constant signal generation. However, the sensitivity of the kit is lower by a factor of 10 as compared to the ATP Bioluminescence Assay Kit HS II, which is recommended for determinations in the high-sensitivity range. The ATP Bioluminescence Assay Kit HS II also contains an efficient cell lysis reagent, and can be used for the detection of ATP in microorganisms or animal cells. The ATP Bioluminescence Assay Kit CLS II has a Detection limit of 10-11 M ATP (10-15 moles), using a luminometer.

Cell Cytometry Assay

In some embodiments, the at least one assay is a cell cytometry assay, and wherein the assay device comprises a micro-laser, a microcomputer, and an optical sensor.

Cell cytometry is a laser-based, biophysical technology employed in cell counting, cell sorting, biomarker detection and protein engineering, by suspending cells in a stream of fluid and passing them by an electronic detection apparatus. It allows simultaneous multiparametric analysis of the physical and chemical characteristics of up to thousands of particles per second. Flow cytometry is routinely used in the diagnosis of health disorders, especially blood cancers, but has many other applications in basic research, clinical practice and clinical trials. A common variation is to physically sort particles based on their properties, so as to purify populations of interest.

As a non-limiting example, a beam of light (usually laser light) of a single wavelength is directed onto a hydrodynamically focused stream of liquid. A number of detectors are aimed at the point where the stream passes through the light beam: one in line with the light beam (Forward Scatter or FSC) and several perpendicular to it (Side Scatter or SSC) and one or more fluorescence detectors. Each suspended particle from 0.2 to 150 micrometers passing through the beam scatters the ray, and fluorescent chemicals found in the particle or attached to the particle may be excited into emitting light at a longer wavelength than the light source. This combination of scattered and fluorescent light is picked up by the detectors, and, by analysing fluctuations in brightness at each detector (one for each fluorescent emission peak), it is then possible to derive various types of information about the physical and chemical structure of each individual particle. FSC correlates with the cell volume and SSC depends on the inner complexity of the particle (i.e., shape of the nucleus, the amount and type of cytoplasmic granules or the membrane roughness). This is because the light is scattered off of the internal components of the cell. Some flow cytometers on the market have eliminated the need for fluorescence and use only light scatter for measurement. Other flow cytometers form images of each cell's fluorescence, scattered light, and transmitted light.

Fluorescence-activated cell sorting (FACS) is a specialized type of flow cytometry. It provides a method for sorting a heterogeneous mixture of biological cells into two or more containers, one cell at a time, based upon the specific light scattering and fluorescent characteristics of each cell. It is a useful scientific instrument, as it provides fast, objective and quantitative recording of fluorescent signals from individual cells as well as physical separation of cells of particular interest.

As a non-limiting example, the cell suspension is entrained in the center of a narrow, rapidly flowing stream of liquid. The flow is arranged so that there is a large separation between cells relative to their diameter. A vibrating mechanism causes the stream of cells to break into individual droplets. The system is adjusted so that there is a low probability of more than one cell per droplet. Just before the stream breaks into droplets, the flow passes through a fluorescence measuring station where the fluorescent character of interest of each cell is measured. An electrical charging ring is placed just at the point where the stream breaks into droplets. A charge is placed on the ring based on the immediately prior fluorescence intensity measurement, and the opposite charge is trapped on the droplet as it breaks from the stream. The charged droplets then fall through an electrostatic deflection system that diverts droplets into containers based upon their charge. In some systems, the charge is applied directly to the stream, and the droplet breaking off retains charge of the same sign as the stream. The stream is then returned to neutral after the droplet breaks off.

In addition to the ability to label and identify individual cells via fluorescent antibodies, cell cytometry can be used to measure cellular products such as cytokines, proteins, and other factors. Similar to ELISA sandwich assays, CBA assays use multiple bead populations typically differentiated by size and different levels of fluorescence intensity to distinguish multiple analytes in a single assay. The amount of the analyte captured is detected via a biotinylated antibody against a secondary epitope of the protein, followed by a streptavidin-R-phycoerythrin treatment. The fluorescent intensity of R-phycoerythrin on the beads is quantified on a flow cytometer equipped with a 488 nm excitation source.

Concentrations of a protein of interest in the samples can be obtained by comparing the fluorescent signals to those of a standard curve generated from a serial dilution of a known concentration of the analyte.

In some embodiments, the at least one assay is an environmental assay selected from air quality assays, asbestos assays, water quality assays, soil content assays, or radon gas assays. In some embodiments, the at least one assay is an environmental assay and the assay device comprises gas chromatography (GC).

Functional Module

Figure 4:
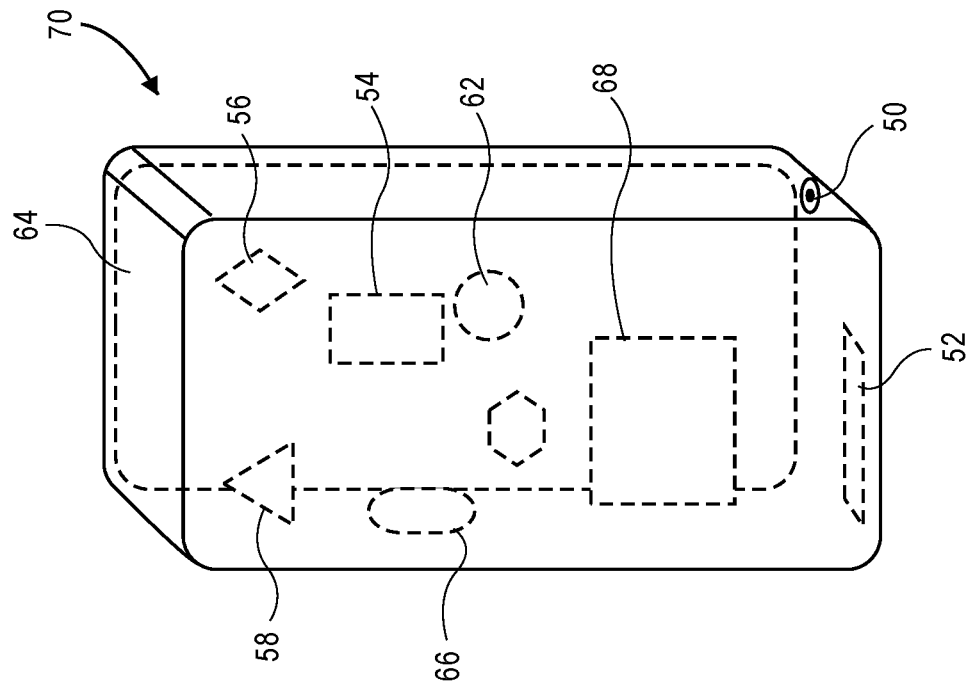
FIG. 4 is a front elevation view of a functional module according to the present disclosure.

Turning now to FIG. 4, a non-limiting example of the functional module 70 is illustrated as including a housing 71, a functional device 72, and a DC port 80 for receiving power. The functional module 70 also includes a connector 82 that is engaged when the connector is positioned within the recessed receiving are 16.

As illustrated in FIG. 4, the functional device 72 includes one or more of a battery 54, a wireless data transmission device 56, a wired data transmission device 58, a microprocessor 68, an interface for receiving and recording signals from at least one vital sign detector 60, a luminescence recorder 62, a display device 64, a portable computing device, a data storage device 66, and combinations thereof.

Battery

In some embodiments, the at least one functional module comprises a battery, and wherein the assay module further comprising a power inlet for receiving electric power from the battery.

By way of non-limiting examples, suitable batteries include primary batteries, rechargeable batteries, wet cells, dry cells, and solar cells. Example types of primary batteries include Alkaline, Lithium-Copper Oxide, Lithium-Iron Disulfide, Lithium-Manganese Dioxide, Mercury Oxide, Nickel Oxyhydroxide, Silver-Oxide, Silver-Zinc, Zinc-air, Zinc-Carbon, and Zinc-Chloride. Non-limiting exemplary types of rechargeable batteries include Lead-acid, NiMH, NiZn, AgZn, and Lithium ion.

Data Tranmission Device

In some embodiments, the at least one functional module comprises a wireless data transmission device. In some embodiments, the wireless data transmission device operates on one or more transmission technologies. Suitable technologies may be 3G communication protocols, 4G communication protocols, GSM standards, CDMA protocols, IEEE 802.11 standards, Bluetooth protocols, satellite communications, visible light communications, infrared communications, and/or near field communications (NFC). In some embodiments, the wireless data transmission device is adapted to transmit date to a local area network or the Internet. In some embodiments, the at least one functional module comprises a wired data transmission device to connect to a local area network or the Internet through wired data transmission.

In accordance with the description herein, suitable devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, and video game consoles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

Microprocessor

In some embodiments, the at least one functional module comprises a microprocessor. In some embodiments, the microprocessors are solo core, dual-core, quad-core, 8-core, 16-core, 32-core, 64-core microprocessors. The microprocessors may be graphic processors with one core or more than one core. In some cases, the microprocessors are microcontrollers and single processors. Alternatively, the microprocessor may be an electronic circuitry designed specifically to process the data described in this subject matter.

Vital Sign Detector Interface

In some embodiments, the at least one functional module comprises an interface for at least one vital sign detector operative associated with the functional module. In some embodiments, the at least one vital sign detectors collects body temperature, heart rate, blood pressure, respiratory rate, or combinations thereof. In some embodiments, the detector may comprise electronic circuitry to read the vital sign data, process the data, and/or store the data. The electronic circuitry may be a controller, a signal processor, or a microprocessor. In further embodiments, the detector may further comprise a mechanical component for collect the vital sign information; by way of a non-limiting example, a tube to receive the volume of respiration.

Luminescence Recorder

In some embodiments, the at least one functional module comprises a luminescence recorder adapted to record luminescence generated by the assay device. In some embodiments, the luminescence recorder is selected from a camera, a fluorescent light recorder, a UV recorder, or combinations thereof. In some embodiments, the luminescence recorder is a built-in camera of a portable computing device. In some embodiment, the luminescence recorder comprises a light source and a light receiver, such as a pin diode/amplifier type receiver tuned to a specific wavelength.

Display Device

In some embodiments, the at least one functional module comprises a display device adapted to display assay module information, functional module information, sample information, or combinations thereof. In some embodiments, the display device is a high-resolution display device. In some embodiments, the high-resolution display device further comprises a touch screen overlay. In some embodiments, the display device is a display window of a portable computing device. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In certain embodiments, the display is a holographic display. In still further embodiments, the display is a combination of devices such as those disclosed herein.

Portable Computing Device

In some embodiments, the portable computing device is selected from a smart-phone or a tablet computer. In some embodiments, the portable computing device comprises a software module configured to provide step-by-step guidance for using the assay apparatus. In some embodiments, the portable computing device comprises a software module configured to collect, process and organize assay information acquired from the assay module, the functional module, or a combination thereof. In some embodiments, the portable computing device comprises software module configured to communicate assay information to a user, wherein the assay information is acquired from the assay module, the functional module, or a combination thereof. In some embodiments, the assay information is securely communicated to the user through a server. In some embodiments, the server is an Internet server or a local access network server. In some embodiments, the user is a patient, a doctor, or a nurse.

Portable computing devices suitable for use in the present disclosure include, but are not limited to, mobile phones, mobile computing devices, smartphones, portable computers, tablet computers, and mobile computers.

Data Storage Device

In some embodiments, the data storage device is configured to store assay information acquired from the assay module, the functional module, or a combination thereof. Suitable storage devices may be a computer readable storage medium that is a tangible component of a digital processing device. In further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Interactive Assay Apparatus

In some embodiments, the assay apparatus according to the present disclosure is an interactive assay apparatus. The interactive assay apparatus comprises an assay module adapted to perform an interactive assay comprising multiple assay steps, and a portable frame adapted to releasably retain the assay module. The assay module comprises a sample receiver, an interactive assay device operatively associated with the sample receiver. The interactive assay device comprises at least one check point adapted to allow selective continuation of the remaining assay steps.

In some embodiments, the interactive assay device comprises an optical device configured to collect assay information the at least one check point. In some embodiments, the optical device generates an image of the at least one check point. In some embodiments, the optical device generates a signal reflecting assay information collected at the check-point.

In some embodiments, the selective continuation of the remaining assay steps is controlled by a user. In some embodiments, the selective continuation of the remaining assay steps is controlled by a microprocessor.

In some embodiments, the interactive assay comprises at least one immunodiagnostic assay. In some embodiments, the interactive assay device comprising microfluidic channels. Without wishing to be bound by any particular theory, it is contemplated that the interactive assay device improves efficiency of the multi-step interactive assay, such as by reducing sample consumption, by reducing assay time, by improving accuracy of assay, or combinations thereof.

Referring now to FIG. 3, a non-limiting example of the interactive assay module 40 is illustrated as including a sample receiver 46 in fluid communication with an interactive assay device 48. The interactive assay device includes microfluidic channels having one or more check points (not shown) and an optical assay device for collecting assay information. The assay module 40 also includes a connector 52 that is engaged when the connector is positioned within the recessed receiving are 16. The assay module 40 further includes an arm 42 having a distal end 43 that is insertable into an adjacent recessed receiving area 16 or directly into a functional module 70. The arm 42 further includes an LCD 44 operatively connect to the optical assay device 48 so that assay information, such as images of the microfluidic channels and/or the check points, can be displayed on LCD 44, and can be further enhanced, analyzed, and/or process by the functional module 70, such as a smartphone or other image processing devices.

Module-Recognizing Mechanism

In some embodiments, the assay apparatus further comprises a module-recognizing mechanism configured to prevent unauthorized use of the assay apparatus. In some embodiments, the module-recognizing mechanism comprises one or more physical features on the assay module and one or more matching physical feature on the portable frame. In some embodiments, the assay module is allowed to perform the at least one assay upon matching of the one or more physical features on the assay module and the portable frame. In some embodiments, the at least one assay module is allowed to perform the interactive assay after matching of the one or more physical features on the assay module and the portable frame and upon breaking of the one or more physical features on the assay module. In some embodiments, the module-recognizing mechanism comprises security hologram, data encryption, or a combination thereof.

Security holograms are difficult to forge because they are replicated from a master hologram which requires expensive, specialized and technologically advanced equipment. In some embodiment, the security hologram used in the assay apparatus can be 2D/3D "hologram" images. This type of security hologram includes two or more images stacked in such a way that each is alternately visible depending upon the angle of perspective of the viewer. These holograms may be of two layers (i.e. with a background and a foreground) or three layers (with a background, a middle ground and a foreground). The matter of the middle ground is usually superimposed over the matter of the background of the hologram. These holograms display a unique multilevel, multi-color effect. These images have one or two levels of flat graphics "floating" above or at the surface of the hologram. The matter in the background appears to be under or behind the hologram, giving the illusion of depth.

Data encryption suitable for use in the present disclosure includes software modules or firmware in the assay module, functional module, or both. In an encryption scheme, the data or information is encrypted using an encryption algorithm, turning it into an unreadable format. This is usually done with the use of an encryption key, which specifies how the data or information is to be encoded. Unauthorized parties, even upon seeing the data or information in the unreadable format, cannot determine the contents of the data or information in its original form. An authorized party, however, is able to decode the unreadable format using a decryption algorithm (usually requires a secret decryption key) that unauthorized parties do not have access to. For technical reasons, an encryption scheme usually needs a key-generation algorithm to randomly produce keys. In some embodiments, the data encryption used in the assay apparatus includes specialized integrated circuits (ICs) with or without software or firmware algorithms.

Example 1

Referring now to FIGS. 6-8, a non-limiting example of the assay apparatus 10 comprises a molded plastic frame 12 that is sized to receive a smartphone 14 (assay device) though an aperture 16. A transparent plastic window 18 on the frame 12 is included for viewing the smartphone screen. As used herein, a "smartphone" is an iPhone, as manufactured by Apple, Inc., or its equivalent, as manufactured by Samsung, Sony, and others. Also, the assay apparatus 10 may be used with an iPad, or other type of computer tablet device. It will be appreciated that different frames 12 may be employed to fit different smartphone, and computer tablet configurations. The assay apparatus 10 may also include a USB port 26 for receiving power, or for receiving USB enabled communication devices for communication with the assay apparatus 10, or for other functions necessary for certain assay modules or smartphone programs (i.e., "apps"). The assay apparatus 10 may also include a DC port 28 to receive power.

As employed in one aspect, the smartphone camera 22 (as shown in FIGS. 6-8) is aligned with the with the assay optical results area of an assay/holder that is received in an assay slot 32 (sample receiver) within the frame 12. Slot 30 in this example is configured to receive a functional module 70 to improve performance of the assay module 40, to supplement the assay module 40, and/or to provide auxiliary functions to the assay apparatus 10 that is not directly related to the operation of the assay module 40. More than one slot 30 can be provided on the frame 12 for multiple functional modules. The functional module 70 in this example includes a functional device 70 selected from a battery, a wireless data transmission device, a wired data transmission device, a microprocessor, an interface for receiving and recording signals from at least one vital sign detector, and combinations thereof. For example, the functional module can be a battery that supplies back-up electrical power to the assay apparatus while the primary power source of the assay apparatus is the battery in the smartphone 14. Alternatively, the functional module can be a battery that functions as primary electrical power source while the battery in the smartphone 14 supplies back-up electrical power. As another example, the functional module can be a wireless data transmission device that supplies back-up wireless data transmission capability to the assay apparatus while the primary wireless data transmission capability is provided by the smartphone 14. Alternatively, the functional module can be a wireless data transmission device that provides primary wireless data transmission capability to the assay apparatus while the smartphone 14 supplies back-up wireless data transmission capability.

In a preferred embodiment, the assay apparatus 10 includes a one or more software modules (e.g. computer software application loaded onto the smartphone) that directs a caregiver to perform a sequence of events. For example, the caregiver would first take the patients photograph, then insert the backside of the assay into the assay slot 32 to verify assay type and record the serial number. Specifically, unique bar or QR codes on the lateral flow format can be read while being inserted into the assay apparatus 10 that configures the user interface. This could also be done with the simpler apparatus shown in FIGS. 5 and 6 as described.

Then, the assay is removed, rotated, and re-inserted into the assay slot 32. The assay results are then read by the smartphone camera 22 and may be electronically, or otherwise transmitted to a doctor, a medical center or a hospital, as well as storing the image of the assay results in the smartphone photo library. Alternatively, the Bluetooth, near field communication, WiFi, 3/4G smartphone capabilities may be used to permanently store data, communicate with other devices, do more sophisticated analysis remotely, or perform other functions.

Besides presenting graphical and alphanumeric test results, the smartphone/iPAD can walk a less skilled healthcare provider or possibly a patient at home through processing the test and saving the results (if that's an option) step-by-step. The display can also provide feedback test progress and results using Augmented Reality (AR) to superimpose imagery and graphics over live images.

The camera 22 photographs the capture line images, and bar/QR codes that represent serial no. /patient no./lot codes/ and other information. For example, a smartphone or iPad can communicate with a network of iPads and/or a secure LAN using a proprietary protocol, Bluetooth, WiFi, or 3G. The assay apparatus 10 stores and retrieves patient information via the physicians' office or hospital wireless LAN (which may employ a HIPPA compliant data and HL7 v2.3 compatible data formatting protocol) using appropriate privacy protocols. In the home setting, the assay apparatus 10 could communicate with a set-top box (acting as a central hub) for presentation of test results on a display monitor (TV or computer), which most patients know how to use. The set-top box can also be used to submit test results to a doctor, enabling remote monitoring, and allowing the physician to remain in control of treatment from the patients' home. All of this is packed into an off-the-shelf smartphone device instead of designing and producing circuit boards, positioning a camera, and writing all the operating code.

As shown in FIG. 7, the assay apparatus 10 includes consumables slot 32 positioned opposite the side of the iPad with the camera to accommodate a proprietary consumable format to perform simple imaging using the camera, and perhaps special light sources to perform different kinds of assays. The simplest light source is the iPad flash. Alternative embodiments may employ an infrared source or a source that would enable fluorescence. The iPad controls everything, and the one or more software modules loaded into the smartphone or iPad does image processing, presentation on the LCD, and communication. The consumable may contain the results of an immunoassay, nucleic acid assay, or some other kind of test that has nothing to do with life science (e.g. an instant asbestos test, a soil content test, radon test). The consumables slot 32 may be employed to handle tests that can be analyzed by image analysis.

Example 2

Referring back to FIG. 2, a non-limiting example of the assay apparatus includes an assay module 40 of a two-piece design. The assay module 40 includes an assay device 48 in the form of a smartphone, and a sample receiver 46 in the form of a sample slot provided on the portable frame 12. The frame 12 includes three recessed receiving areas 16: one on the front of the portable frame for receiving the smartphone, one the side of the portable frame for receiving a functional module 70, and another on the side of the portable frame (shown without module inserted therein) for receiving either another functional module 70 or another assay module 40.

In this example, the functional module 70 is an interface of a vital sign detector 60. In use, an assay sample is inserted into the sample receiver 46, and assay information is collected by the assay device 48, such as by using the built-in camera of the smartphone as the optical assay device. At the same time, the viral sign detector interface 60 is inserted into one of the recessed receiving area 16 on the side of the portable frame 12 for collecting vital sign information of the patient. Alternatively, the vital sign collection can be completed prior to, or after, the collection of assay information by the assay device 48. The wired or wireless connection between the vital sign detector interface 60 and the assay device 48 (smartphone) allows the vital sign information to be transferred to the smartphone, combined with the assay information, and transmitted to a nurse or physician. The smartphone can also include one or more software modules to display the vital sign information, and/or the assay information, to provide the user or patient with immediate feedback.

Example 3

Still referring to FIG. 2, a non-limiting example of the assay apparatus includes an assay module 40 of a two-piece design. The assay module 40 includes an assay device 48 in the form of a smartphone, and a sample receiver 46 in the form of a sample slot provided on the portable frame 12. The frame 12 includes three recessed receiving areas 16: one on the front of the portable frame for receiving the smartphone, one the side of the portable frame for receiving a functional module 70, and another on the side of the portable frame (shown without module inserted therein) for receiving either another functional module 70 or another assay module 40.

In this example, the functional module 70 comprises a microprocessor 68 that replaces, expands, or supplements the computing or processing capability of the assay module 40. In this regard, the assay device 48 (smartphone) may function only as an optical device that collects initial assay information (such as images of the assay sample). The initial assay information is then transmitted, through wired or wireless data transmission between the functional module 70 and the assay module 40, to the microprocessor 68 for computing, analysis, enhancement or other data processing functions. The processed assay information is then transferred back to the assay device 48 (smartphone), and is transmitted to a nurse or physician thereafter. The smartphone can also include one or more software modules to display the initial and/or processed assay information to provide the user or patient with immediate feedback. Alternatively, the functional module 70 also includes a wireless data transmission device 56 through which processed assay information can be directly transmitted to a nurse or physician. In another alternative, a second functional module 70 that includes a wireless data transmission device 56 is inserted to the remaining recessed receiving area 16 on the side of the portable frame 12 (shown as empty in FIG. 2) to provide or enhance data transmission capability of the assay apparatus 10.

Example 4

Referring now to FIG. 1, a non-limiting example of the assay apparatus includes an assay module 40 of a one-piece design. The assay apparatus 10 also includes a functional module 70 in the form of a smartphone. While a sample slot provided on the portable frame 12, the sample receiver 46 in this example is provided on the assay module 40. The frame 12 includes three recessed receiving areas 16: one on the front of the portable frame for receiving the smartphone, one the side of the portable frame for receiving the assay module 40, and optionally another on the side of the portable frame for receiving either another functional module 70 or another assay module 40.

In this example, the functional module 70 (smartphone) functions as a battery 54, a wireless data transmission device 56, a wired data transmission device 58, a display device 64, a data storage device 66, a microprocessor 68, or combinations thereof. In use, an assay sample is loaded on the sample receiver 46 of the assay module 40, and the assay device (e.g. optical device, bioluminescence device, chromatography device, or electrophoresis device) collects initial assay information. The initial assay information is then transferred, through wired or wireless data transmission, to the functional module 70 (smartphone), where one or more software modules operate the smartphone to process the initial assay information, to transmit the processed assay information to a nurse or a physician, and/or to display the initial and/or processed assay information to the user or patient for immediate assay feedback.

Example 5

Still referring to FIG. 1, a non-limiting example of the assay apparatus includes an assay module 40 of a one-piece design. The assay apparatus 10 also includes a functional module 70 in the form of a smartphone. While a sample slot provided on the portable frame 12, the sample receiver 46 in this example is provided on the assay module 40. The frame 12 includes three recessed receiving areas 16: one on the front of the portable frame for receiving the smartphone, one the side of the portable frame for receiving the assay module 40, and optionally another on the side of the portable frame for receiving either another functional module 70 or another assay module 40.

A second functional module 70 (not show) is also retained by the portable frame 12 to supplement or enhance the smartphone. In this example, the second module 70 comprises a microprocessor 68 that replaces, expands, or supplements the computing or processing capability of the smartphone. In this example, the smartphone functions as a battery 54, a wireless data transmission device 56, a wired data transmission device 58, a display device 64, a data storage device 66, or combinations thereof. In use, the initial assay information collected by the assay device 48 can be transferred to the second functional module 70, where the intial assaty information is processed by the microprocessor 48. The processed information is then transferred to the smartphone, and is transmitted to a nurse or physician thereafter. The smartphone can also include one or more software modules to display the initial and/or processed assay information to provide the user or patient with immediate feedback.

Alternatively, the second functional module 70 also includes a wireless data transmission device 56 through which processed assay information can be directly transmitted to a nurse or physician. In another alternative, a third functional module 70 that includes a wireless data transmission device 56 is inserted to another recessed receiving area 16 on the side of the portable frame 12 (not shown in FIG. 1) to provide or enhance data transmission capability of the assay apparatus 10. In those embodiment, the use of the smartphone as a functional module is optional.

Example 6

Still referring to FIG. 1, a non-limiting example of the assay apparatus includes an assay module 40 of a one-piece design. The assay apparatus 10 also includes a functional module 70 in the form of a smartphone. While a sample slot provided on the portable frame 12, the sample receiver 46 in this example is provided on the assay module 40. The frame 12 includes three recessed receiving areas 16: one on the front of the portable frame for receiving the smartphone, one the side of the portable frame for receiving the assay module 40, and optionally another on the side of the portable frame for receiving either another functional module 70 or another assay module 40.

A second functional module 70 (not show) is also retained by the portable frame 12 to provide additional functions that is not directly related to the assay module. In this example, the second functional module 70 comprises an interface of a vital sign detector 60. In use, an assay sample is inserted into the sample receiver 46, and assay information is collected by the assay device 48. At the same time, the vital sign detector interface 60 is inserted into one of the recessed receiving area 16 on the side of the portable frame 12 for collecting vital sign information of the patient. Alternatively, the vital sign collection can be completed prior to, or after, the collection of assay information by the assay device 48. The wired or wireless connection between the vital sign detector interface 60 and the smartphone allows the vital sign information to be transferred to the smartphone, combined with the assay information (transferred to the smartphone from the assay device 40), and transmitted to a nurse or physician. The smartphone can also include one or more software modules to display the vital sign information, and/or the assay information, to provide the user or patient with immediate feedback.

Example 7

Figure 9:
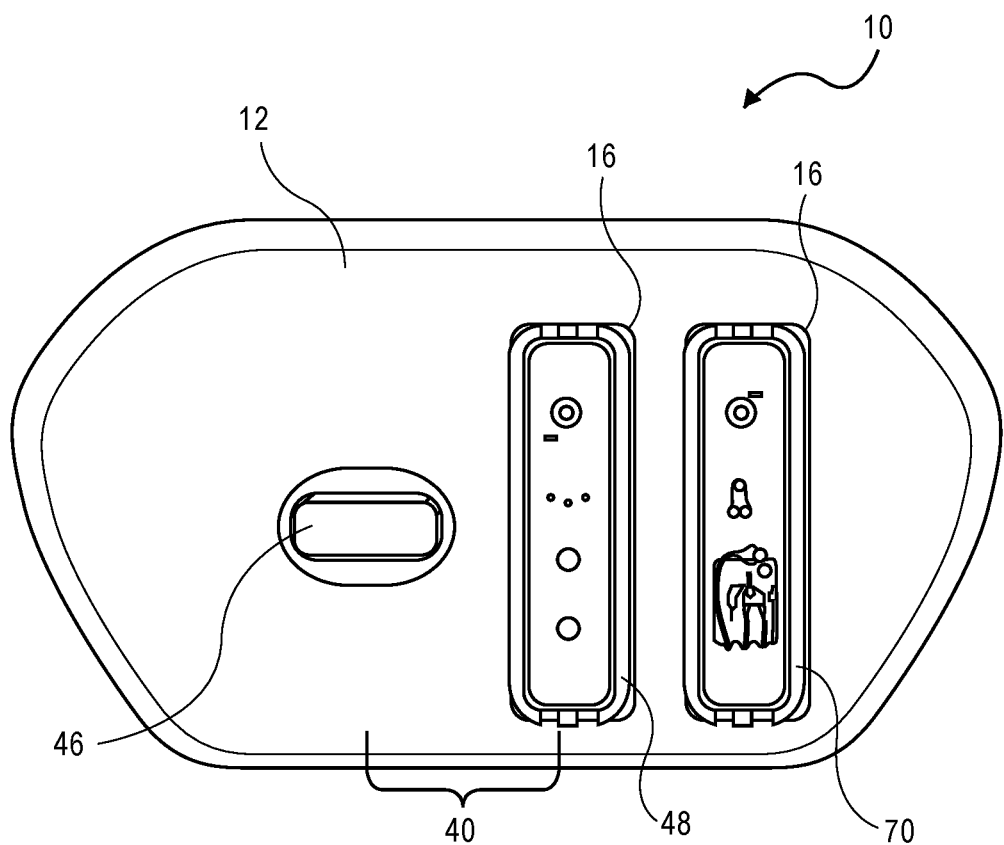
FIG. 9 is a side perspective view of an assay apparatus according to the present disclosure.

Turning now to FIG. 9, a non-limiting example of the assay apparatus 10 includes an assay module 40 of a two-piece design. The assay module 40 includes an optical assay device 48 inserted into a recessed receiving area 16 provided on the portable frame 12, and a sample receiver 46 in the form of a sample slot provided on the portable frame 12. The frame 12 includes three recessed receiving areas 16: one on the front of the portable frame for receiving the smartphone that may or may not be used in this example, one on the side of the portable frame for receiving the optical assay device 48, and another on the side of the portable frame for optionally receiving either another functional module 70 (shown) or another assay module 40 (not shown).

In this example, the sample receiver 46 and optical assay device 48 are optically connected with each other, such as through one or more light channels, one or more optical fiber connectors, one or more optical lenses, or combinations thereof. The functional module can be another optical assay device that provides additional or enhanced optical assay or analysis. In this regards, the assay module 40 and the functional module 70 are also optically connected with each other, such as through one or more light channels, one or more optical fiber connectors, one or more optical lenses, or combinations thereof. Alternatively, the functional module 70 can include a microprocessor to provide the computing or processing capability of the assay apparatus 10, and a wireless data transmission device 56 through which processed assay information can be directly transmitted to a nurse or physician. In this regard, a smartphone is not necessary but can be optionally used as a display to provide a user interface. In another alternative, a smartphone can be used to provide the processing and data transmission functions of the assay apparatus 10.

Without wishing to be bound by any particular theory, it is contemplated that the technical features of the present disclosure, including the assay module, functional module, portable frame, interactive assay module, module-recognizing mechanism, or various combinations thereof, and their integration into a portable device, allows improved portability, improved efficiency, improved adaptability, improved accuracy, and/or improved security of existing on-site assay apparatus and methods.

For example, the disclosed assay apparatus can provide accurate analysis of the level of drug concentration in the patient sample. The assay apparatus takes the guess work out of quantification, and also provides a means for storing patient test results in a secure place with the rest of the patients' medical history. As another example, the disclosed assay apparatus further improves the precision of quantitative diagnostics by performing the steps of the assay that is conventionally performed by central laboratory instruments.

In those embodiments that utilize smartphone or other portable computing device in the assay module or functional module, the user interface and wireless communications are completely supplied by that flexible device, thereby reducing cost and improving efficiency of the assay platform. For example, existing (non-wireless) POCT assay apparatus utilizes built-in display device, input devices, data transmission devices, the cost of which can be reduced in the disclosed assay apparatus, using smartphone or portable computing device to supply the user interface and wireless control. Moreover, the smartphone or portable computing device has a built-in camera to functional as the optical assay device or to seamlessly integrate patient information into the record. Further, the smartphone or portable computing device is 3G/4G ready, in addition to Bluetooth, v802.11, and near field communications, thereby allowing the assay apparatus to communicate assay or patient information through direct phone calls or through electronic data communication. Finally, the smartphone or portable computing device has a high resolution display that is capable of direct display of photos and high resolution graphics.

The foregoing is illustrative of the present disclosure, and is not to be construed as limiting thereof. While embodiments of the present invention have been indicated and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. An assay apparatus, comprising:
   at least two assay modules, each assay module comprising an assay device adapted to perform a different assay on a sample;
   a portable frame adapted to receive the at least two assay modules simultaneously; and
   a functional module configured for wireless data transmission and operably associated with each assay module when received.

2. The assay apparatus of claim 1, further comprising another functional device selected from the group consisting of a battery, a wired data transmission device, a microprocessor, an interface for receiving and recording signals from at least one vital sign detector, a luminescence recorder, a display device, a portable computing device, and a data storage device.

3. The assay apparatus of claim 2, wherein the another functional module comprises the battery, and wherein the at least two assay modules further comprise a power inlet for receiving electric power from the battery.

4. The assay apparatus of claim 2, wherein the another functional module comprises the wired data transmission device and connects to a local area network or the Internet through wired data transmission.

5. The assay apparatus of claim 2, wherein the another functional module comprises the portable computing device.

6. The assay apparatus of claim 5, wherein the portable computing device is a smart phone or a tablet computer.

7. The assay apparatus of claim 2, wherein the another functional module comprises the microprocessor.

8. The assay apparatus of claim 7, wherein the microprocessor is a quad-core microprocessor.

9. The assay apparatus of claim 2, wherein the another functional module comprises the interface for at least one vital sign detector operative associated with the functional module.

10. The assay apparatus of claim 9, wherein the at least one vital sign detector collects body temperature, heart rate, blood pressure, respiratory rate, or combinations thereof.

11. The assay apparatus of claim 2, wherein the another functional module comprises a luminescence recorder adapted to record luminescence generated by the assay device.

12. The assay apparatus of claim 11, wherein the luminescence recorder is selected from a camera, a fluorescent light recorder, a UV recorder, a diode/amplifier type receiver, or combinations thereof.

13. The assay apparatus of claim 12, wherein the luminescence recorder is a built-in camera of a portable computing device.

14. The assay apparatus of claim 2, wherein the another functional module comprises the display device adapted to display assay module information, functional module information, sample information, or combinations thereof.

15. The assay apparatus of claim 14, wherein the display device is a high-resolution display device.

16. The assay apparatus of claim 15, wherein the high-resolution display device further comprises a touch screen overlay.

17. The assay apparatus of claim 1, wherein the wireless data transmission operates on one or more transmission technologies selected from the group consisting of 3G communication protocols, 4G communication protocols, GSM standards, CDMA protocols, IEEE 802.11 standards, Bluetooth protocols, satellite communications, visible light communications, infrared communications, and near field communications.

18. The assay apparatus of claim 1, wherein the wireless data transmission transmits date to a local area network or the Internet.

* * * * *